(12) United States Patent
Tseng et al.

(10) Patent No.: US 9,345,431 B2
(45) Date of Patent: May 24, 2016

(54) METHOD AND OPTICAL SYSTEM FOR EVALUATING CONCENTRATIONS OF COMPONENTS IN TISSUE

(71) Applicant: National Cheng Kung University, Tainan (TW)

(72) Inventors: Sheng-Hao Tseng, Tainan (TW); Chao-Kai Hsu, Tainan (TW); Shih-Yu Tzeng, Kaohsiung (TW); Nan-Yu Cheng, Tainan (TW)

(73) Assignee: National Cheng Kung University, Tainan (TW)

( * ) Notice: Subject to any disclaimer, the term of this patent is extended or adjusted under 35 U.S.C. 154(b) by 196 days.

(21) Appl. No.: 13/944,697

(22) Filed: Jul. 17, 2013

(65) Prior Publication Data
US 2014/0206957 A1 Jul. 24, 2014

(30) Foreign Application Priority Data

Jan. 18, 2013 (TW) .............................. 102101950 A

(51) Int. Cl.
*A61B 5/00* (2006.01)
*A61B 5/1455* (2006.01)

(52) U.S. Cl.
CPC ............... *A61B 5/443* (2013.01); *A61B 5/1455* (2013.01)

(58) Field of Classification Search
CPC ......... A61B 5/00; A61B 5/443; A61B 5/1455
USPC ......................................... 600/407, 473–476
See application file for complete search history.

(56) References Cited

U.S. PATENT DOCUMENTS

| 5,931,779 A | * | 8/1999 | Arakaki et al. ............... 600/310 |
| 6,016,435 A | * | 1/2000 | Maruo et al. .................. 600/316 |
| 2009/0318815 A1 | * | 12/2009 | Barnes et al. ................. 600/473 |

FOREIGN PATENT DOCUMENTS

TW          201208648 A       3/2012

* cited by examiner

*Primary Examiner* — Peter Luong
(74) *Attorney, Agent, or Firm* — Muncy, Geissler, Olds & Lowe, P.C.

(57) ABSTRACT

A method and an optical system for evaluating the spatial distribution of the concentrations of components in tissue are disclosed. The novel detecting probe included in the optical system comprises plural optical fiber sets, each optical fiber set respectively comprises at least one source optical fiber and at least one detector optical fiber, the source optical fiber connects with the multi-wavelength light source, the source optical fiber delivers light from the multi-wavelength light source onto a tested tissue; and the angle between one optical fiber set and another optical fiber set is greater than 0° and less than and not equal to 180°. Through the optical system of the present invention, the spatial distribution of the concentrations of components such as water, hemoglobin, melanin, lipid, and collagen in the tested tissue can be derived by an equation (I) defined in the present specification.

18 Claims, 7 Drawing Sheets

METHOD AND OPTICAL SYSTEM FOR EVALUATING CONCENTRATIONS OF COMPONENTS IN TISSUE

CROSS REFERENCE TO RELATED APPLICATION

This application claims the benefits of the Taiwan Patent Application Serial Number 102101950, filed on Jan. 18, 2013, the subject matter of which is incorporated herein by reference.

BACKGROUND OF THE INVENTION

1. Field of the Invention

The present invention relates to a method and an optical system for evaluating concentrations of components in tissue and, more particularly, to a method and an optical system with a novel probe for evaluating concentrations and distributions of components in tissue.

2. Description of Related Art

As the techniques of the medical science developed, more and more means have been applied to evaluate conditions (e.g. the concentrations, and distributions) of various components in tissues. In fact, understanding of the component conditions may improve the treating modalities, effects, and safety of medical treatments.

Furthermore, to understand the component conditions in tissues, several methods are developed, and one of the effective conventional methods is the slide examination. However, the slide examination is an invasive examination, and the wound for getting the slice may turn into scars on skin. Hence, some participants may not accept the aforementioned disadvantages. In order to decrease the drawbacks caused by the invasive detection, some research teams have developed noninvasive manners to evaluate the component conditions in tissues.

Among the developed noninvasive manners, diffuse reflectance spectroscopy (DRS) technique and multi-photon microscopy have been employed to characterize the conditions as well as the optical properties of tissue in vivo. Although the multi-photon microscopy can provide structural information of tissues in vivo, this technique has disadvantages of long measurement time and high system cost. On the other hand, different from the multi-photon microscopy, DRS is a simple and low-cost technique, which can provide macroscopic information, such as scattering property, collagen concentration, lipid concentration, melanin concentration and hemoglobin concentration, of tissue samples.

Collagen is one rich component in skin, which is highly related to the formations of scars including normal scars, hypertrophic scars and keloids. Keloid is a skin disease occurred as a result of abnormal wound healing and is characterized by extending beyond the borders of the original wound. Moreover, keloid does not regress, and usually recur after excision. The pathogenesis of keloids is complex and involves both genetic and environmental factors. Hypertrophic scars are similar to keloid, but are confined to the wound borders and usually regress over time. The predominant extracellular matrix (ECM) component of keloid and hypertrophic scar is collagen.

Although the predominant ECM component of keloids and hypertrophic scars is collagen, the pathology thereof is still slightly different. For example, collagen fibers in keloids are larger, thicker and wavier than in hypertrophic scars or normal scars. However, the current detecting method still cannot accurately identify the differences between hypertrophic scars and keloids.

Hence, in order to provide proper treatment modalities to keloids, identification of differences between hypertrophic scars, keloids and normal scars are a key factor for finding the correct therapeutical method. Through the evaluation of skin chromophores, including water, hemoglobin, and collagen, identification of differences between hypertrophic scars, keloids and normal scars can be evaluated accurately to assist in in vivo keloid diagnosis. In addition, the evaluation of skin chromophores can apply on various grounds such as clinical treatment or biomedical science for monitoring the condition of normal skin and for evaluating the status of pathological skin. Clinical or skin micro-cosmetic surgeries are held in accordance with the evaluated content of skin chromophores by lesion development or aging. The absorption spectra of skin were utilized to calculate the chromophore concentrations and monitor the hemodynamics of dermis.

Therefore, there is a need for device and method which can detect the conditions of components in a tested tissue, such as collagen concentration, in a quick, accurate, and cheap way, which have potential applications in skin disease detection and the evaluation of effect of skin care or cosmetic dermatology.

SUMMARY OF THE INVENTION

The object of the present invention is to provide a method for evaluating the collagen concentration of tissues. In addition, other tissue chromophores, such as melanin, hemoglobin, and water can be extracted in the same time. More particularly, the method of the present invention can quantify the concentrations of the aforementioned components in a noninvasive way quickly and accurately.

Another object of the present invention is to provide an optical system for evaluating the spatial distribution of the concentrations of the aforementioned components, which can be co-operated with the method of the present invention.

To achieve the aforementioned object, the method for evaluating concentrations of components in a tissue of the present invention comprises the following steps: (A) illuminating a tested tissue with light from a multi-wavelength light source, in which the light passes into the tested tissue; (B) detecting reflected light from the tested tissue with a detector in multiple directions to obtain diffuse reflectance spectra; (C) converting the diffuse reflectance spectra into absorption spectra; and (D) fitting the absorption spectra with known chromophore absorption spectra to derive concentrations of components in the tested tissue by an equation (I) represented as follows:

$$\mu_a(\lambda) = C_{HbO2}\mu_a^{HbO2}(\lambda) + C_{Hb}\mu_a^{Hb}(\lambda) + C_{Melanin}\mu_a^{Melanin}(\lambda) + C_{Water}\mu_a^{Water}(\lambda) + C_{Fat}\mu_a^{Fat}(\lambda) + C_{Collagen}\mu_a^{Collagen}(\lambda) \quad (I)$$

wherein $\mu_a(\lambda)$ is a total absorption coefficient, $\mu_a^{HbO2}(\lambda)$ is an absorption coefficient of oxygenated hemoglobin, $\mu_a^{Hb}(?)$ is an absorption coefficient of deoxygenated hemoglobin, $\mu_a^{Melanin}(\lambda)$ is an absorption coefficient of melanin, $\mu_a^{Water}(\lambda)$ is an absorption coefficient of water, $\mu_a^{Fat}(\lambda)$ is an absorption coefficient of lipid, $\mu_a^{Collagen}(\lambda)$ is an absorption coefficient of collagen, $C_{HbO2}$ is a concentration of oxygenated hemoglobin, $C_{Hb}$ is a concentration of deoxygenated hemoglobin, $C_{Melanin}$ is a concentration of melanin, $C_{Water}$ is a concentration of water, $C_{Fat}$ is a concentration of lipid, is and $C_{Collagen}$ is a concentration of collagen.

In the method of the present invention, the concentrations of the components are derived by obtaining the absorption spectra and reduced scattering spectra from the diffuse reflectance spectra reflected from the tested tissue and then fitting the absorption spectra with the known chromophore absorption spectra, in which the known chromophore absorption spectra include absorption spectra of melanin, hemoglobin, collagen, fat and water. Especially, the basic algorism for linearly fitting the obtained absorption spectra with the known chromophore absorption spectra to extract the concentration of each component is based on Beer's law, in which the obtained absorption spectra is the sum of the products of the concentration and the absorption coefficient of each component including melanin, hemoglobin, collagen, fat and water to obtain the total absorption coefficient of all the detected components of the detected tissue. It should be noted that the method of the present invention can evaluate the collagen concentration, so the method of the present invention can be applied for various collagen-related studies, such as skin-collagen-related studies. For example, the method of the present invention can be applied evaluate the conditions of skin diseases and the efficacy of skin cosmetic treatments, as well as diagnose the types and the severity of skin diseases.

In the method of the present invention, the tested tissue is not particularly limited, and can be any organ. Preferably, the tested tissue examined by the method of the present invention is superficial tissue. More preferably, the tested tissue is skin. Herein, the detected depth of the skin may be ranged from 0.1 cm to 0.2 cm, and preferably from 0.1 cm to 0.15 cm.

In the case that the method of the present invention is applied to detect the collagen concentration of the skin, it is possible to evaluate the severity of skin disease comprising normal scar, hypertrophic scar, keloid, vitiligo, or soriasis, or the efficacy of cosmetic dermatology or skin care comprising wrinkle-removal, spot-removal, or whitening, but the present invention is not limited thereto.

In the method of the present invention, the detected components including melanin, hemoglobin, collagen, fat and water have almost 100% absorption regarding to the wavelength range of the multi-wavelength light source ranging from 400 nm to 2500 nm. Hence, the wavelength range of the multi-wavelength light source used in the step (A) of the method of the present invention is not particularly limited, as long as it overlaps with or locates within the aforementioned range from 400 nm to 2500 nm. Preferably, the wavelength thereof is in a range from 150 nm to 3500. More preferably, the wavelength thereof is in a range from 200 nm to 3200 nm, 350 nm to 3000 nm, 450 nm to 2500 nm, 550 nm to 1800 nm, 650 nm to 1500 nm, 500 nm to 1300 nm, 600 nm to 1000 nm, or 700 nm to 900 nm. Most preferably, the wavelength thereof is in a range from 700 nm to 860 nm.

In the method of the present invention, the detector is separated from the multi-wavelength light source by a predetermined distance. Preferably, the distance between the detector and the multi-wavelength light source is less than 5 mm. More preferably, the distance therebetween is less than 3.5 mm. Most preferably, the distance therebetween is less than 2.5 mm.

The steps (A) and (B) of the method of the present invention may be alternately performed for several times, and the interval between two performing times are not particularly limited and can be adjusted according to the examination requirement. In one aspect of the present invention, the distance between the detector and the multi-wavelength light source verified with time, so as to ensure that the all detected photons are diffused and have passed into the tested tissue. In another aspect of the present invention, the light from the multi-wavelength light source is illuminated onto the tested tissue at a direction defined by source-detector pair(s). In other words, the direction means a linear direction connected through the source optical fiber(s) and the detector optical fiber(s). If necessary, two or more directions also can be applied to understand the distribution of the components of the tested tissue and further improve the examination accuracy of the method of the present invention. Therefore, two or more source-detector pairs can be provided according to actual conditions of the tested tissue or the accuracy requirement for the evaluation purpose. In order to ensure the illuminating direction of the multi-wavelength light source, the method of the present invention may further comprise a step (A0) before the step (A): positioning the light emitting from the multi-wavelength light source on the tested tissue with an alignment unit.

In the case that the light from the multi-wavelength light source is illuminated onto the tested tissue at two directions, the method of the present invention may further comprise a step (E) after the step (D): obtaining a ratio of the concentration of one of the components measured at a first direction to that measured at a second direction by an equation (II) represented as follows:

$$R=(C_V/C_P)-1 \qquad (II)$$

wherein R is the ratio of the concentration of the component measured at the first direction to that measured at the second direction, $C_V$ is the concentration of the component measured at the first direction, $C_P$ is the concentration of the component measured at the second direction, and both $C_V$ and $C_P$ are one of $C_{HbO2}$, $C_{Hb}$, $C_{Melanin}$, $C_{Water}$, $C_{Fat}$, and $C_{Collagen}$. Preferably, the one of the components is collagen, and both $C_V$ and $C_P$ are $C_{Collagen}$. In addition, an angle included between the first direction and the second direction may be greater than 0° and less than and not equal to 180°. Preferably, the angle is in a range from 30° to 150°. More preferably, the angle is in a range from 45° to 135°. Most preferably, the angle is around 90°, i.e. the first direction is vertical to the second direction.

Additionally, in the method of the present invention, the first direction and the second direction may be respectively vertical and parallel to a major axis of a scar on skin, a direction of muscle fibers, or a tensile line of skin, but the present invention is not particularly limited thereto. Herein, the term "major axis" preferably means a longitude axis of the scare on skin. Preferably, the first direction and the second direction are respectively vertical and parallel to a major axis of a scar on skin.

In one preferred aspect of the method of the present invention, the equation (II) is used to obtain the ratio of the collagen concentration measured at the first direction to that measured at the second direction, and preferably the first direction and the second direction may be respectively vertical and parallel to a major axis of a scar on skin.

In addition, the aforementioned method of the present invention can be applied on any optical system having the same measuring concept, and one example optical system is provided in the present invention.

The optical system for evaluating concentrations of components in a tissue, comprising: a multi-wavelength light source, a detecting probe, an alignment unit, and a detecting device. Herein, the detecting probe comprises at least one optical fiber set, each optical fiber set respectively comprises at least one source optical fiber and at least one detector optical fiber, the source optical fiber connects with the multi-wavelength light source to deliver light from the multi-wavelength light source onto a tested tissue. The alignment unit is disposed on the detecting probe. In addition, the detecting device such as a spectrometer is coupled to the detector optical fiber to receive reflected light from the tested tissue to obtain diffuse reflectance spectra.

In the optical system of the present invention, the detector optical fiber is separated from the source optical fiber by a predetermined distance. In the optical system of the present invention, the distances between each source optical fiber and each detector optical fiber is less than 5 mm; more preferably less than 3.5 mm; and most preferably less than 2.5 mm.

In addition, in the optical system of the present invention, the novel detecting probe comprises plural optical fiber sets, and an angle included between the detector optical fiber of one optical fiber set and the detector optical fiber of another optical fiber set is greater than 0° and less than and not equal to 180°. Preferably, the angle between the detector optical fiber of one optical fiber set and the detector optical fiber of another optical fiber set is 90°. In one aspect of the optical system of the present invention, detecting probe comprises two optical fiber sets arranged perpendicularly to each other.

Other objects, advantages, and novel features of the invention will become more apparent from the following detailed description when taken in conjunction with the accompanying drawings.

DETAILED DESCRIPTION OF THE PREFERRED EMBODIMENT

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

The following embodiments of the present invention demonstrated the detective accuracy of the method and the optical device of the present invention via quantifying the collagen contents at keloid sites and normal sites of the tested skin.

Figure 1:
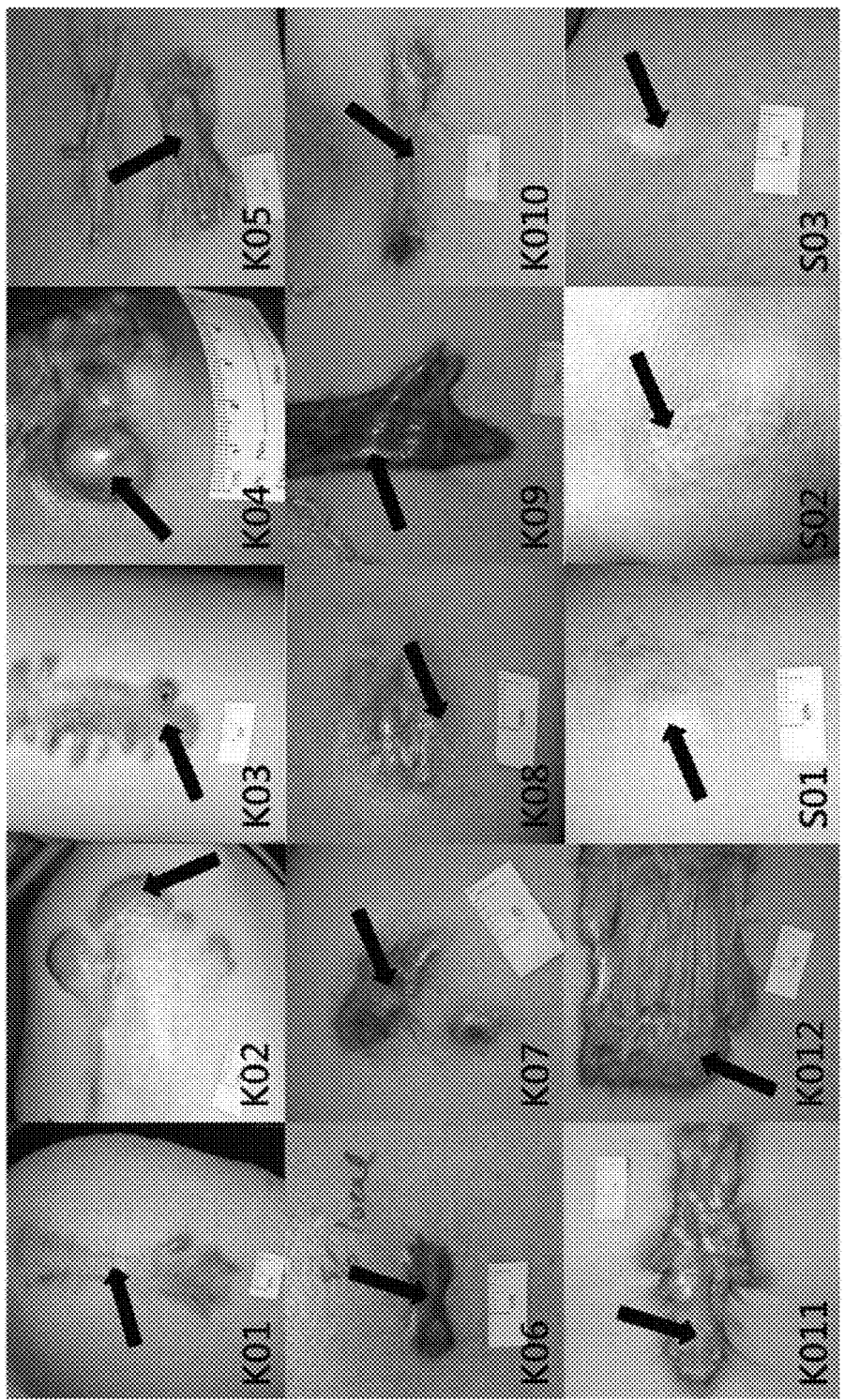
FIG. 1 is photos showing scar sites in a preferred embodiment of the present invention.

In the present embodiment, twelve subjects with keloid scars, and three subjects with normal scars were recruited in the National Cheng Kung University Hospital. The protocol was approved by the Institutional Review Board, and written informed consent was obtained from all subjects prior to the measurements. The photos of the scar sites of the subjects recruited in this study are illustrated in FIG. 1. Arrows in FIG. 1 point to the scar measurement sites. Subjects labeled K1 to K12 are those diagnosed with keloid scars and subjects labeled S1 to S3 are those with normal scars. For each subject, measurements were taken at two sites, including one site at the active lesion of the pathological scar, which was usually in the margin of the keloid (S), and one normal skin site (N), which was 3 cm apart from the border of scar.

Figure 2:
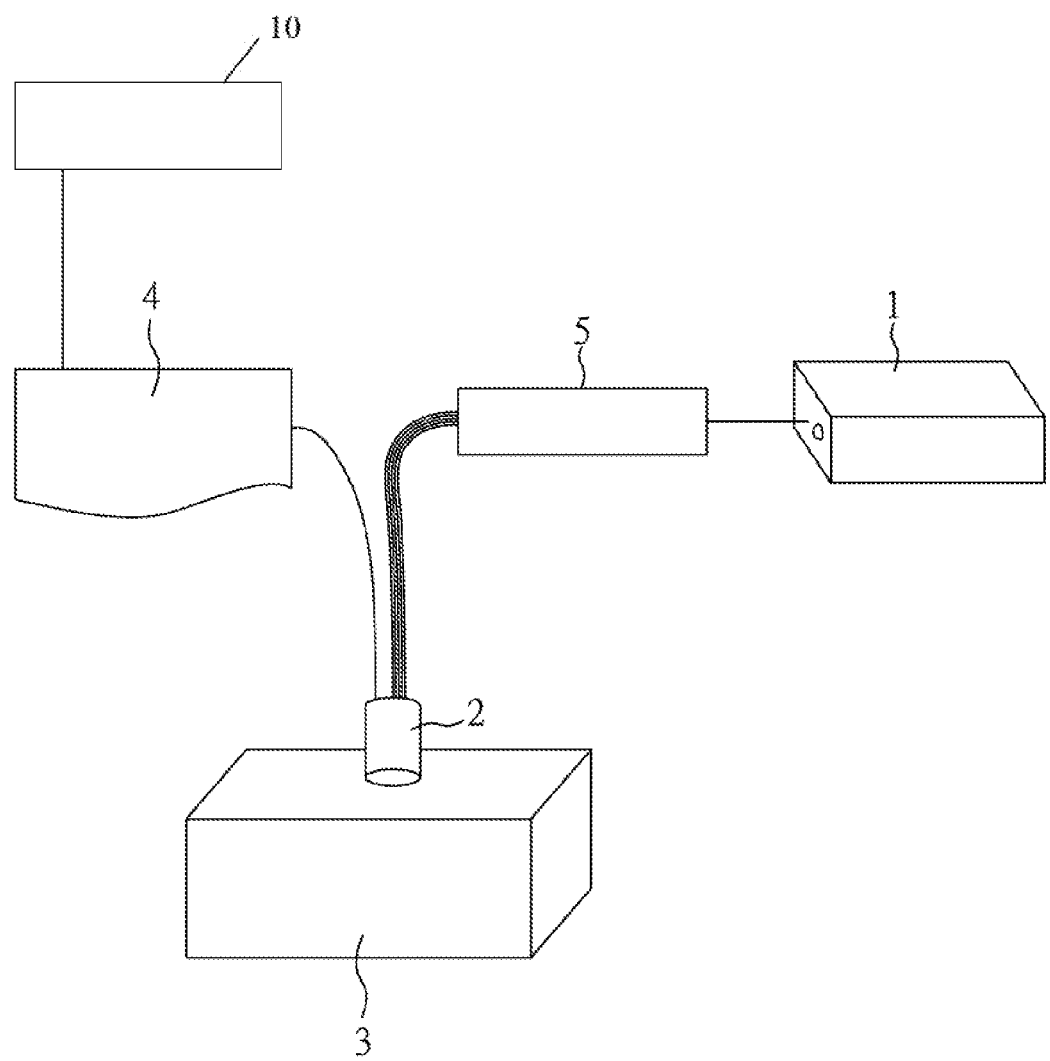
FIG. 2 is a perspective view of the optical system according to a preferred embodiment of the present invention.
Figure 3:
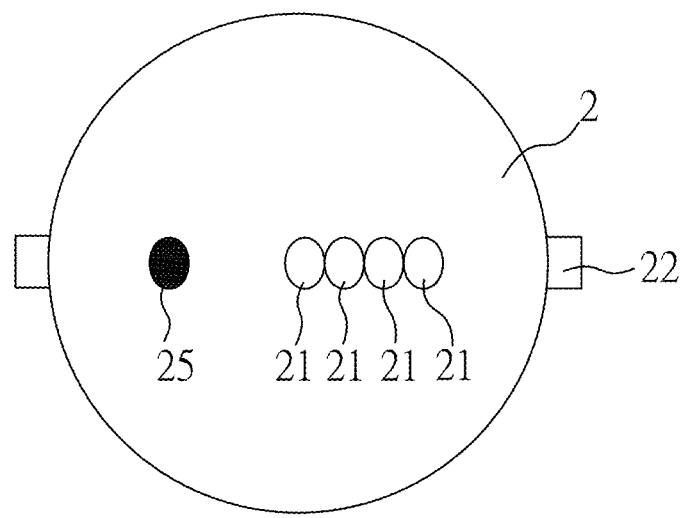
FIG. 3 is a cross-sectional view of the probe according to a preferred embodiment of the present invention.
Figure 4:
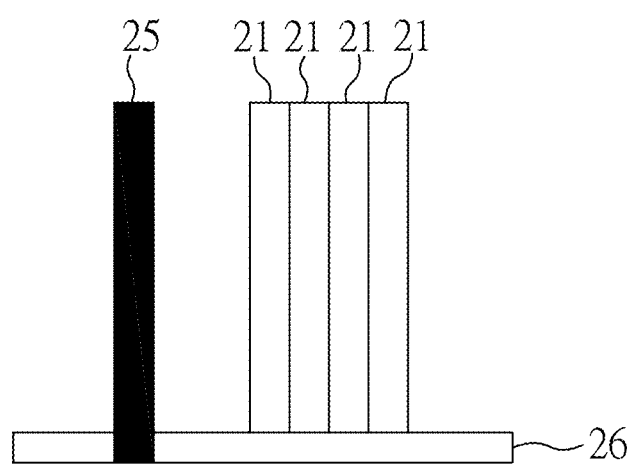
FIG. 4 is a longitudinal-sectional view of the probe according to a preferred embodiment of the present invention.

The optical system used in the present embodiment is shown in FIGS. 2-4. The optical system of the present embodiment comprises: a multi-wavelength light source 1, a detecting probe 2, an alignment unit 22 disposed on the detecting probe 2, and a detecting device 4.

In optical device of the present embodiment, the detecting device 4 is a spectrometer equipped with a back-thinned CCD (QE65000, Ocean Optics, Fla.). The multi-wavelength light source is multi-wavelength Tungsten Halogen light source (HL2000, Ocean Optics, Fla.). Additionally, the diffuser 26 is the high scattering Spectralon (Labshpere, N.H.), which has a diameter of 6.5 mm and a thickness of 1 mm.

In addition, the detecting probe 2 comprises one optical fiber set comprising four source optical fibers 21 and one detector optical fiber 25, and one end of each source optical fiber 21 connects with the multi-wavelength light source 1 to deliver light from the multi-wavelength light source 1 onto tested skin 3. In addition, the detecting device 4 is coupled to the detector optical fiber 25 to receive reflected light from the tested skin 3 to obtain diffuse reflectance spectra. The source optical fibers 21 and the detector Optical fiber 25 employed in the detecting probe 2 are multimode fibers with 440-µm core diameter and 0.22 numerical aperture. However, single mode fibers may also be used as the source optical fibers 21 and the detector optical fiber 25 in other embodiment of the present invention.

Furthermore, the optical device of the present embodiment further comprises a optical switch 5 (Piezosystem Jena, Germany), bridged the source optical fibers 21 connecting to the multi-wavelength light source 1, in order to control one of the four source optical fibers 21 of the detecting probe 2 deliver light at a time.

Moreover, as shown in FIG. 2 and FIG. 4, the detecting probe 2 of the present embodiment further comprises a diffuser 26 interposed between the source optical fibers 21 and the tested tissue 3. More specifically, the detector optical fiber 25 penetrates the diffuser 26 to that it is flush with the lower surface of the diffuser 26; and the source optical fibers 21 placed on the upper surface of the diffuser 26. Furthermore, as shown in FIG. 3, the source optical fibers 21 and the detector optical fiber 25 are disposed in a linear arrangement, and the distances between the four source optical fibers 21 and the detector optical fiber 25 are 2.88, 2.4, 1.92, and 1.44 mm, respectively.

The detecting device 4 and the optical switch 5 are connected to a laptop computer 10 and are coordinated and controlled by a graphic user interface developed based on Labview (National Instruments, TX). At each measurement, four reflectance spectra associated with four source-detector pairs are sequentially acquired and stored into one file. The average time required to take one complete measurement is about 10 s. Due to limited light intensity of the multi-wavelength light source 1 and spectral range of the detecting device 4, the diffuse reflectance spectra acquired in this study is within 550 to 860 nm range.

Figure 5:
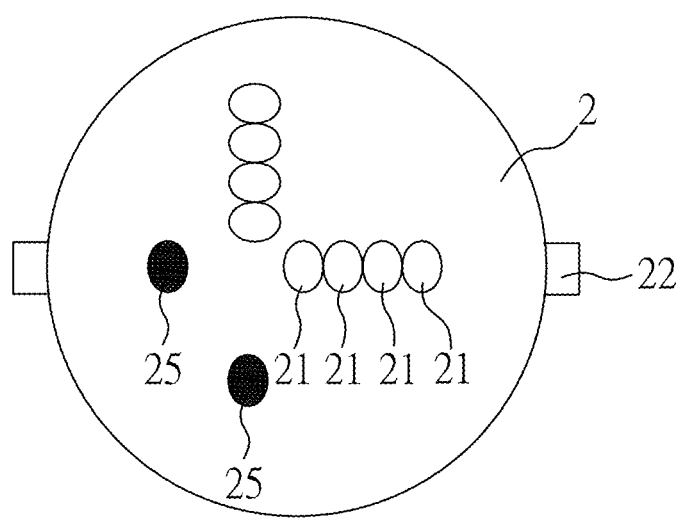
FIG. 5 is a cross-sectional view of the probe according to another preferred embodiment of the present invention.
Figure 6:
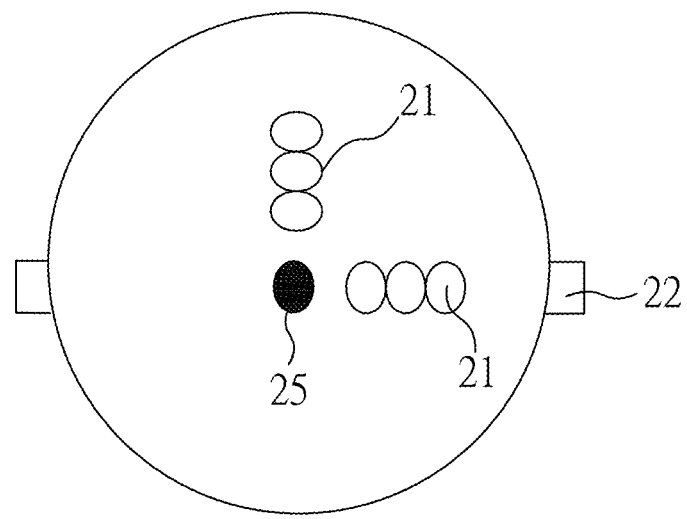
FIG. 6 is a cross-sectional view of the probe according to another preferred embodiment of the present invention.
Figure 7:
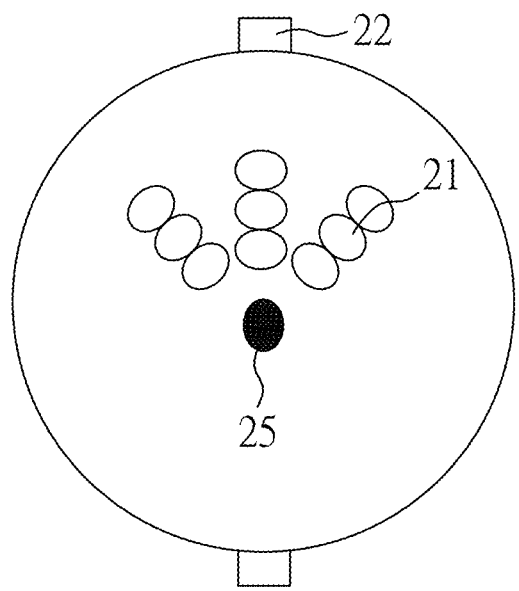
FIG. 7 is a cross-sectional view of the probe according to another preferred embodiment of the present invention.

In other embodiments, the aforementioned detecting probe 2 can comprise multiple fiber sets. As shown in FIGS. 5-7, the detecting probe 2 comprises two optical fiber sets arranged perpendicularly to each other (FIG. 5); or comprises two optical fiber sets arranged perpendicularly to each other and shared with the same detector optical fiber 25 (FIG. 6); or comprises three optical fiber sets shared with the same detector optical fiber 25, in which the arranged angles between three optical fiber sets can be the same or different (FIG. 7).

Hereinafter, the method for evaluating concentrations of components in skin by using the optical system of the present embodiment is described.

First, as shown in FIG. 1 and FIG. 2, the detecting probe 2 the optical system used in the present embodiment was placed on the sites pointed by arrows on the tested skin and the measurement directions were defined as the optical fiber alignment of the detecting probe 2 parallel (P) or vertical (V) to the major axis of a scar via the alignment unit 22 of the detecting probe 2.

Next, as shown in FIGS. 2-4, the tested tissue 3 (i.e. scars, keloids or normal skin) was irradiated with light from the multi-wavelength light source 1. The light emitting from the multi-wavelength light source 1 was delivered via the one of the four source optical fibers 21, and passed through the diffusor 26 of the detecting probe 2 onto the tested tissue 3. Herein, the diffusor 26 can effectively diffuse the photons coming from the source optical fibers 21 before they hit the tested tissue 3. Then, the detector optical fiber 25 delivered reflected light from the tested tissue 3 in multiple directions to the detecting device 4 via the detector optical fiber 25.

The aforementioned steps (i.e. illuminating light and detecting reflected light) were performed for four times, to sequentially collect the reflected light from the tested tissue 3 irradiated with the light from the multi-wavelength light source 1 via the other three source optical fibers 21.

After the aforementioned process, diffuse reflectance spectra was obtained. Then, the obtained diffuse reflectance spectra were converted into absorption spectra and reduced scattering spectra.

The reduced scattering spectra were fit to the scattering power law ($\mu'_s = a*\lambda^{-b}$) to obtain "a" and "-b" parameters and to smooth the raw scattering spectra. The parameters "a" and "A" represent the magnitude of scattering and the wavelength in nanometer, respectively. The wavelength exponent "-b" characterizes the mean size of the tissue scatters and defines spectral behavior of the reduced scattering coefficient.

The absorption spectra were fit linearly with known chromophore absorption spectra, including melanin, hemoglobin ($HbO_2$), collagen, fat and water by organelle, to extract the concentrations of melanin, hemoglobin ($HbO_2$), collagen, fat and water in the tested tissue.

$$\mu_a(\lambda) = C_{HbO2}\mu_a^{HbO2}(\lambda) + C_{Hb}\mu_a^{Hb}(\lambda) + C_{Melanin}\mu_a^{Melanin}(\lambda) + C_{Water}\mu_a^{Water}(\lambda) + C_{Fat}\mu_a^{Fat}(\lambda) + C_{Collagen}\mu_a^{Collagen}(\lambda) \quad (I)$$

wherein $\mu_a(\lambda)$ is a total absorption coefficient, $\mu_a^{HbO2}(\lambda)$ is an absorption coefficient of oxygenated hemoglobin, $\mu_a^{Hb}(\lambda)$ is an absorption coefficient of deoxygenated hemoglobin, $\mu_a^{Melanin}(\lambda)$ is an absorption coefficient of melanin, $\mu_a^{Water}(\lambda)$ is an absorption coefficient of water, $\mu_a^{Fat}(\lambda)$ is an absorption coefficient of lipid, $\mu_a^{Collagen}(\lambda)$ is an absorption coefficient of collagen, $C_{HbO2}$ is a concentration of oxygenated hemoglobin, $C_{Hb}$ is a concentration of deoxygenated hemoglobin, $C_{Melanin}$ is a concentration of melanin, $C_{Water}$ is a concentration of water, $C_{Fat}$ is a concentration of lipid, and $C_{Collagen}$ is a concentration of collagen.

Figure 8:
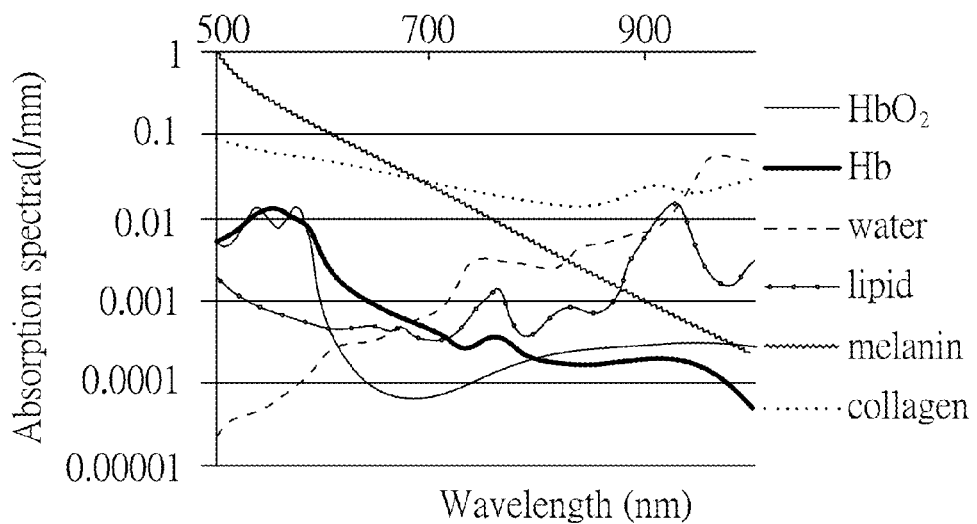
FIG. 8 shows known chromophore absorption spectra used in a preferred embodiment of the present invention.
Figure 9:
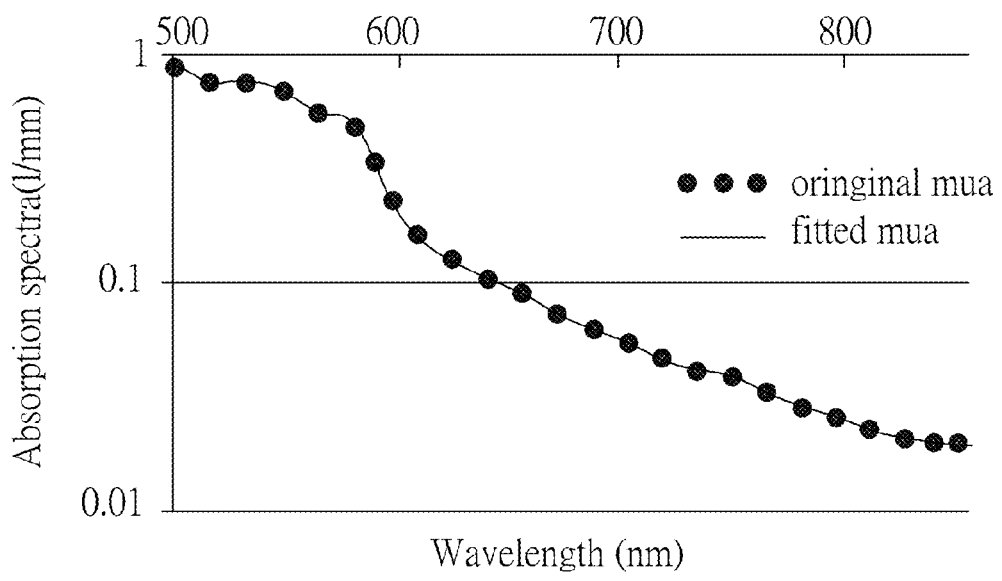
FIG. 9 shows total absorption spectra of one tested skin obtained in a preferred embodiment of the present invention.

For example, FIG. 8 shows the known chromophore absorption spectra including $10^{-4}$ of pure melanosome containing melanin, 1 μM of hemoglobin ($HbO_2$), collagen, fat and water used in the present embodiment. FIG. 9 shows the absorption spectra of one tested tissue obtained in the present embodiment, wherein all data (original $\mu_a$) were obtained by summing the products of the concentration and the absorption coefficient of each component separately and fitting with the aforementioned known chromophore absorption spectra at the same wavelength.

Figure 10:
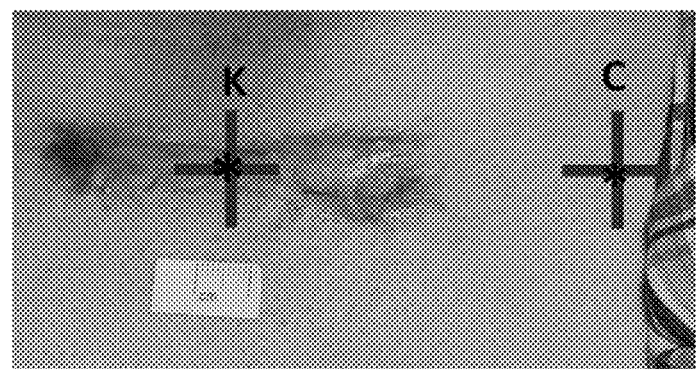
FIG. 10 is a photo showing a scar measurement in a preferred embodiment of the present invention.

In the present embodiment, the collagen concentrations of K01 to K12 and S01 to S03 were obtained by the optical system shown in FIG. 2 to FIG. 4, and the results are listed in Table 1 and Table 2. Table 3 also shows the ratio of the collagen measured at a first direction to that measured at a second direction by an equation (II) represented as follows:

$$R = (C_V/C_P) - 1 \quad (II)$$

wherein R is the ratio of the collagen concentrations measured at the first direction vertical to the major axis of the scar to that measured at the second direction parallel to the major axis of the scar, and $C_V$ and $C_P$ are $C_{Collagen}$ respectively measured at the directions vertical and parallel to the major axis of the scar on the tested skin. The definition of the first direction (V) and the second direction (P) are shown in FIG. 10.

TABLE 1

| Tested skin | V/P | VSS | Collagen (%) S | Collagen (%) N | Melanin (%) S | Melanin (%) N | HbO$_2$ (μM) S | HbO$_2$ (μM) N | Hb (μM) S | Hb (μM) N | $\mu'_{s800}$ (mm$^{-1}$) S | $\mu'_{s800}$ (mm$^{-1}$) N | -b S | -b N |
|---|---|---|---|---|---|---|---|---|---|---|---|---|---|---|
| K01 | V | 5 | 26.33 | 19.95 | 0.04 | 0.04 | 4.565 | 3.64 | 7.18 | 3.15 | 1.55 | 1.55 | −1.76 | −1.7 |
| K02 | V | 9 | 24.8 | 23.28 | 0.17 | 0.14 | 0 | 0.78 | 6.63 | 2.98 | 1.44 | 1.61 | −2 | −1.44 |
| K03 | V | 7 | 26.33 | 22.31 | 0.16 | 0.08 | 28.17 | 2.28 | 48.09 | 2.37 | 0.9 | 1.62 | −2.04 | −1.4 |
| K04 | V | 10 | 30.07 | 31.73 | 0.17 | 0.19 | 0.33 | 4.59 | 10.22 | 5.35 | 1.27 | 1.44 | −1.69 | −1.18 |
| K05 | V | 8 | 36.86 | 28.41 | 0.08 | 0.07 | 11.39 | 6.64 | 12.51 | 2.56 | 1.34 | 1.57 | −1.64 | −1.44 |
| K06 | V | 4 | 49.47 | 27.3 | 1.59 | 0.06 | 80.31 | 6.01 | 59.18 | 4.07 | 1.39 | 1.88 | −1.52 | −1.66 |
| K07 | V | 8 | 47.67 | 26.88 | 0.26 | 0.11 | 0 | 2.13 | 18.02 | 2.97 | 1.18 | 1.32 | −1.74 | −1.69 |
| K08 | V | 5 | 36.17 | 27.3 | 0.14 | 0.12 | 14.31 | 3.56 | 9.02 | 2.93 | 1.52 | 1.57 | −1.51 | −1.68 |
| K09 | V | 8 | 43.23 | 19.82 | 0.33 | 0.1 | 0 | 0.88 | 11.36 | 2.44 | 0.97 | 1.69 | −1.42 | −20.5 |
| K10 | V | 5 | 40.46 | 25.77 | 0.73 | 0.22 | 67.21 | 6.67 | 42.5 | 10.8 | 1.68 | 1.78 | −1.4 | −1.97 |
| K11 | V | 10 | 30.9 | 23 | 0.09 | 0.1 | 0.27 | 1.23 | 7.37 | 3.37 | 1.15 | 1.63 | −2.16 | −1.83 |
| K12 | V | 9 | 43.93 | 26.05 | 0.5 | 0.15 | 14.66 | 6.58 | 50.49 | 6.15 | 0.99 | 1.4 | −2.14 | −1.51 |
| S01 | V | 1 | 44.76 | 28.13 | 0.55 | 0.14 | 19.6 | 4.65 | 29.35 | 6.59 | 1.13 | 1.71 | −1.43 | −1.44 |
| S02 | V | 1 | 37 | 29.93 | 0.12 | 0.09 | 6.81 | 2.49 | 4.8 | 2.18 | 1.59 | 1.67 | −1.4 | −1.56 |
| S03 | V | 1 | 29.79 | 28.96 | 0.07 | 0.08 | 1.51 | 3.03 | 3.04 | 3.33 | 1.75 | 1.72 | −2.06 | −1.54 |

TABLE 2

| Tested skin | V/P | VSS | Collagen (%) S | Collagen (%) N | Melanin (%) S | Melanin (%) N | HbO$_2$ (μM) S | HbO$_2$ (μM) N | Hb (μM) S | Hb (μM) N | $\mu'_{s800}$ (mm$^{-1}$) S | $\mu'_{s800}$ (mm$^{-1}$) N | -b S | -b N |
|---|---|---|---|---|---|---|---|---|---|---|---|---|---|---|
| K01 | P | 5  | 16.77 | 23.14 | 0.03 | 0.08 | 6.62  | 3.35  | 6.25  | 2.94  | 1.46  | 1.46 | −1.67 | −1.85 |
| K02 | P | 9  | 22.45 | 23.56 | 0.2  | 0.14 | 0.28  | 1.82  | 12.52 | 4.16  | 1.17  | 1.5  | −2.11 | −1.55 |
| K03 | P | 7  | 22.03 | 19.68 | 0.09 | 0.07 | 36.52 | 1.5   | 59.44 | 1.88  | 0.89  | 1.47 | −2.33 | −1.67 |
| K04 | P | 10 | 23    | 31.73 | 0.11 | 0.16 | 0.21  | 14.49 | 7.35  | 8.04  | 1.34  | 1.39 | −1.99 | −1.2  |
| K05 | P | 8  | 22.17 | 23.14 | 0.06 | 0.05 | 6.17  | 3.03  | 8.08  | 3.33  | 0.89  | 1.29 | −1.81 | −1.93 |
| K06 | P | 4  | 30.21 | 23.56 | 0.37 | 0.05 | 72.41 | 3.18  | 69.13 | 3.11  | 0.86  | 1.78 | −1.87 | −1.89 |
| K07 | P | 8  | 33.53 | 24.94 | 0.16 | 0.11 | 0.4   | 2.44  | 9.69  | 3.12  | 0.94  | 1.18 | −1.86 | −1.84 |
| K08 | P | 5  | 26.19 | 27.44 | 0.07 | 0.13 | 10.6  | 4.07  | 6.07  | 4.46  | 1.43  | 1.54 | −1.57 | −1.64 |
| K09 | P | 8  | 27.99 | 21.62 | 0.23 | 0.1  | 0     | 0.56  | 7.08  | 2.07  | 1.04  | 1.72 | −1.99 | −2.12 |
| K10 | P | 5  | 19.82 | 22.73 | 0.12 | 0.19 | 2.94  | 7.94  | 5.78  | 11.5  | 1.8   | 1.66 | −2.18 | −2.13 |
| K11 | P | 10 | 26.47 | 21.76 | 0.09 | 0.08 | 0     | 1.44  | 5.64  | 3.22  | 1.02  | 1.75 | −20.7 | −2.01 |
| K12 | P | 9  | 29.1  | 23.28 | 0.52 | 0.12 | 18.6  | 5.45  | 58.34 | 9.34  | 0.92  | 1.33 | −2.32 | −1.77 |
| S01 | P | 1  | 33.26 | 30.9  | 0.13 | 0.1  | 4.88  | 8.3   | 10.11 | 7.92  | 1.34  | 1.74 | −1.56 | −1.36 |
| S02 | P | 1  | 39.08 | 30.07 | 0.11 | 0.11 | 6.34  | 4.12  | 5.4   | 4.5   | 1.67  | 1.78 | −1.48 | −1.37 |
| S03 | P | 1  | 30.76 | 27.3  | 0.09 | 0.08 | 1.34  | 4.48  | 3.54  | 2.99  | 1.65  | 1.73 | −1.98 | −1.45 |

TABLE 3

| Tested skin | VSS | Collagen (R = \|C$_P$/C$_P$ − 1\|) S | Collagen (R = \|C$_P$/C$_P$ − 1\|) N | Average collagen (%) S | Average collagen (%) N | Average SaO$_2$ (μM) S | Average SaO$_2$ (μM) N | Average $\mu'_{s800}$ (mm$^{-1}$) S | Average $\mu'_{s800}$ (mm$^{-1}$) N | Average -b S | Average -b N |
|---|---|---|---|---|---|---|---|---|---|---|---|
| K01 | 5  | 0.57 | 0.14 | 21.55 | 21.55 | 45.30 | 52.99 | 1.51 | 1.51 | −1.72 | −1.78 |
| K02 | 9  | 0.10 | 0.01 | 23.63 | 23.42 | 1.32  | 25.30 | 1.31 | 1.56 | −2.06 | −1.50 |
| K03 | 7  | 0.19 | 0.13 | 24.18 | 21.00 | 36.36 | 46.33 | 0.90 | 1.55 | −2.19 | −1.54 |
| K04 | 10 | 0.31 | 0.00 | 26.54 | 31.73 | 3.02  | 54.89 | 1.31 | 1.42 | −1.84 | −1.19 |
| K05 | 8  | 0.66 | 0.23 | 29.52 | 25.78 | 40.62 | 59.72 | 1.12 | 1.43 | −1.73 | −1.69 |
| K06 | 4  | 0.64 | 0.16 | 39.84 | 25.43 | 53.43 | 54.43 | 1.13 | 1.83 | −1.70 | −1.78 |
| K07 | 8  | 0.42 | 0.08 | 40.60 | 25.9  | 1.29  | 42.59 | 1.06 | 1.25 | −1.80 | −1.77 |
| K08 | 5  | 0.38 | 0.01 | 31.18 | 27.37 | 61.69 | 51.10 | 1.48 | 1.56 | −1.54 | −1.66 |
| K09 | 8  | 0.54 | 0.08 | 35.61 | 20.72 | 0.00  | 31.97 | 1.01 | 1.71 | −1.71 | −2.09 |
| K10 | 5  | 1.04 | 0.13 | 30.14 | 24.25 | 48.55 | 39.14 | 1.43 | 1.72 | −1.79 | −2.05 |
| K11 | 10 | 0.17 | 0.06 | 28.69 | 22.38 | 0.98  | 28.79 | 1.09 | 1.69 | −2.12 | −1.92 |
| K12 | 9  | 0.51 | 0.12 | 36.52 | 24.67 | 23.87 | 44.61 | 0.96 | 1.37 | −2.23 | −1.64 |
| S01 | 1  | 0.35 | 0.11 | 39.01 | 29.52 | 36.94 | 46.14 | 1.24 | 1.73 | −1.50 | −1.40 |
| S02 | 1  | 0.05 | 0.00 | 38.04 | 30.00 | 55.26 | 50.68 | 1.63 | 1.73 | −1.44 | −1.47 |
| S03 | 1  | 0.03 | 0.06 | 30.28 | 28.13 | 30.19 | 53.77 | 1.70 | 1.73 | −2.02 | −1.50 |

With reference to Table 1 to Table 3, "VSS" means the Vancouver Scar Scale; −b means the scattering power and the higher value thereof represents the smaller particle; "S" means the keloid site pointed by the arrows as shown in FIG. 1; and "N" means the normal skin site which was 3 cm apart from the keloid site pointed by the arrows as shown in FIG. 1. Table 3 lists average values of various parameters including collagen concentration ratio R and oxygen saturation value (SaO$_2$).

According to the results listed in Tables 1-3, the collagen concentration of tested tissue (i.e. normal scars, keloids and normal skin) can be detected by the optical system of the present embodiment, and quantified by fitting with the algorism represented by the equation (I) as shown in the method of the present embodiment. Additionally, the results shown in Tables 1-3 also demonstrate that the collagen content in the keloid site is certainly higher than that in the normal skin and the normal scar.

Furthermore, when the measurement directions vertical and parallel to the major axis of the scar are taken into consideration, the data shown in Table 3 indicate that the R value of the normal skin approaches "0", and the R values of keloid are significantly higher than those of normal skin. The larger R value indicates the higher severity of the scars. In addition, the data shown in Table 3 also could reveal the anisotropy of the collagen orientation in which higher R values represent higher degree of anisotropy. These results indicate that at least two orthogonal measurement directions are more effective for robustly distinguishing keloids from normal skin, compared to the data obtained from one measurement direction.

Although the present invention has been explained in relation to its preferred embodiment, it is to be understood that many other possible modifications and variations can be made without departing from the spirit and scope of the invention as hereinafter claimed.

What is claimed is:

1. A method for evaluating concentrations of components in a tissue, comprising the following steps:
    (A) providing an optical system for evaluating concentrations of components in a tissue, comprising:
    a multi-wavelength light source;
    a detecting probe comprising at least one optical fiber set and a diffuser, wherein each optical fiber set respectively comprises at least two source optical fibers and at least one detector optical fiber, and source-to-detector distances in each optical fiber set are different, the source optical fibers connect with the multi-wavelength light source, the source optical fibers deliver light from the multi-wavelength light source onto a tested tissue via the diffuser, and the detector optical fiber penetrates the diffuser to receive the diffused light from the source optical fibers as reflected by the tested tissue;
an aligner disposed on the detecting probe for positioning a light emitting from the multi-wavelength light source on the tested tissue;
a detecting device coupled to the detector optical fiber to receive reflected light from the tested tissue to obtain diffuse reflectance spectra; and
an output device connected to the detecting device;
(B) illuminating a tested tissue with light from the multi-wavelength light source, in which the light passes into the tested tissue;
(C) detecting reflected light from the tested tissue with the detecting device coupled to the detector optical fiber to receive reflected light from the tested tissue to obtain diffuse reflectance spectra;
(D) converting the diffuse reflectance spectra into absorption spectra;
(E) fitting the absorption spectra with known chromophore absorption spectra to derive concentrations of components in the tested tissue by an equation (I) represented as follows:

$$\mu_a(\lambda) = C_{HbO2}\mu_a^{HbO2}(\lambda) + C_{Hb}\mu_a^{Hb}(\lambda) + C_{Melanin}\mu_a^{Melanin}(\lambda) + C_{Water}\mu_a^{Water}(\lambda) + C_{Fat}\mu_a^{Fat}(\lambda) + C_{Collagen}\mu_a^{Collagen}(\lambda) \quad (I)$$

wherein $\mu_a(\lambda)$ is a total absorption coefficient, $\mu_a^{HbO2}(\lambda)$ is an absorption coefficient of oxygenated hemoglobin, $\mu_a^{Hb}(\lambda)$ is an absorption coefficient of deoxygenated hemoglobin, $\mu_a^{Melanin}(\lambda)$ is a absorption coefficient of melanin, $\mu_a^{Water}(\lambda)$ is an absorption coefficient of water, $\mu_a^{Fat}(\lambda)$ is an absorption coefficient of lipid, $\mu_a^{Collagen}(\lambda)$ is an absorption coefficient of collagen, $C_{HbO2}$ is a concentration of oxygenated hemoglobin, $C_{Hb}$ is a concentration of deoxygenated hemoglobin, $C_{Melanin}$ is a concentration of melanin, $C_{Water}$ is a concentration of water, $C_{Fat}$ is a concentration of lipid, and $C_{collagen}$ is a concentration of collagen;
(F) obtaining a ratio of the concentration of one of the components measured at a first direction to that measured at a second direction by an equation (II) represented as follows:

$$R = (C_v/C_p) - 1 \quad (II)$$

wherein R is the ratio of the concentration of the component measured at the first direction to that measured at the second direction, $C_v$ is the concentration of the component measured at the first direction, $C_p$ is the concentration of the component measured at the second direction, and both $C_v$ and $C_p$ are one of $C_{HbO2}$, $C_{Hb}$, $C_{Melanin}$, $C_{Water}$, $C_{Fat}$, and $C_{Collagen}$; and
(G) outputting the ratio of the concentration of the component using the output device,
wherein the ratio of the concentration for scar or keloid is higher than the ratio of the concentration for normal skin.

2. The method as claimed in claim 1, wherein the tissue is skin.

3. The method as claimed in claim 1, further comprising a step (A0) before the step (A): positioning the light emitting from the multi-wavelength light source on the tested tissue with an alignment unit.

4. The method as claimed in claim 1, wherein the one of the components is collagen, and both $C_v$ and $C_p$ are $C_{collagen}$.

5. The method as claimed in claim 1, wherein an angle included between the first direction and the second direction is greater than 0° and less than and not equal to 180°.

6. The method as claimed in claim 5, wherein the first direction is vertical to the second direction.

7. The method as claimed in claim 1, wherein the first direction and the second direction are respectively vertical and parallel to a major axis of a scar on skin.

8. The method as claimed in claim 1, wherein the first direction and the second direction are respectively vertical and parallel to a direction of muscle fibers.

9. The method as claimed in claim 1, wherein the first direction and the second direction are respectively vertical and parallel to a tensile line of skin.

10. The method as claimed in claim 1, wherein the detector is separated from the multi-wavelength light source by a predetermined distance.

11. The method as claimed in claim 10, wherein the predetermined distance is less than 5 mm.

12. An optical system for evaluating concentrations of components in a tissue, comprising:
a multi-wavelength light source;
a detecting probe comprising at least one optical fiber set and a diffuser, wherein each optical fiber set respectively comprises at least two source optical fibers and at least one detector optical fiber, source-to-detector distances in each optical fiber set are different, the source optical fibers connect with the multi-wavelength light source, the source optical fibers deliver light from the multi-wavelength light source onto a tested tissue via the diffuser, and the detector optical fiber penetrates the diffuser to receive the diffused light from the source optical fibers as reflected by the tested tissue;
an aligner disposed on the detecting probe for positioning a light emitting from the multi-wavelength light source on the tested tissue; and
a detecting device coupled to the detector optical fiber to receive reflected light from the tested tissue to obtain diffuse reflectance spectra.

13. The optical system as claimed in claim 12, wherein the detector optical fiber is separated from the source optical fibers by a predetermined distance.

14. The optical system as claimed in claim 13, wherein the predetermined distance is less than 5 mm.

15. The optical system as claimed in claim 12, wherein the detecting probe comprises plural optical fiber sets, wherein a first line extending through the source optical fibers and the detector optical fiber of a first optical fiber set are disposed in a linear arrangement, a second line extending through the source optical fibers and the detector optical fiber of a second optical fiber set are disposed in a linear arrangement, and an angle between the first and second optical fiber sets is greater than 0° and less than and not equal to 180°.

16. The optical system as claimed in claim 15, wherein the angle between the first and second optical fiber sets is 90°.

17. The optical system as claimed in claim 12, wherein the detecting probe comprises the first and second optical fiber sets arranged perpendicularly to each other.

18. The optical system as claimed in claim 12, wherein the detecting device is a spectrometer.

* * * * *